United States Patent [19]

Becker et al.

[11] Patent Number: 4,849,590

[45] Date of Patent: Jul. 18, 1989

[54] ELECTRIC SWITCH WITH COUNTERACTING ELECTRO-ELECTRO-DYNAMIC FORCES

[75] Inventors: James A. Becker, Grafton; Lawrence F. Freitag, Bayside, both of Wis.; Frank W. Kussy, Randallstown, Md.

[73] Assignee: Kohler Company, Kohler, Wis.

[21] Appl. No.: 176,718

[22] Filed: Apr. 1, 1988

[51] Int. Cl.[4] ...................... A01H 33/18; A01H 33/20

[52] U.S. Cl. .................................. 200/147 R; 335/16; 335/195; 335/201; 200/144 R; 200/9; 200/10

[58] Field of Search ................... 200/147 R, 144 R, 9, 200/10, 11; 335/16, 195, 11, 201

[56] References Cited

U.S. PATENT DOCUMENTS

| | | | |
|---|---|---|---|
| 1,762,604 | 6/1930 | Ainsworth . | |
| 1,958,159 | 5/1934 | Bresson | 200/87 |
| 2,318,488 | 5/1943 | Hunter et al. | 200/10 |
| 2,821,594 | 1/1958 | Latour | 335/195 |
| 2,944,129 | 7/1960 | Cole et al. | 335/16 |
| 3,092,699 | 6/1963 | Latour | 200/147 R |
| 3,238,326 | 3/1966 | Frey | 200/87 |
| 3,593,227 | 7/1971 | Mitskevich et al. | 335/16 |
| 3,887,888 | 6/1975 | Bayles et al. | 335/195 |
| 3,936,782 | 2/1976 | Moakler et al. | 335/161 |
| 3,949,333 | 4/1976 | Freitag et al. | 335/132 |
| 3,958,095 | 5/1976 | Zaffrann et al. | 200/293 |
| 4,001,738 | 1/1977 | Terracol et al. | 335/16 |
| 4,021,678 | 5/1977 | Moakler et al. | 307/64 |
| 4,086,460 | 4/1978 | Gillette | 200/144 R |
| 4,168,407 | 9/1979 | Wiktor | 200/18 |
| 4,278,958 | 7/1981 | Kandatsu | 335/16 |
| 4,467,301 | 8/1984 | Goodrich | 335/195 |
| 4,511,774 | 4/1985 | Forsell | 200/147 |
| 4,654,490 | 3/1987 | Leone et al. | 200/147 R |

FOREIGN PATENT DOCUMENTS

| | | | |
|---|---|---|---|
| 291253 | 7/1971 | U.S.S.R. | 335/195 |

OTHER PUBLICATIONS

P. 3 of catalog 1100 from the Automatic Switch Company dated 1982.

*Primary Examiner*—Robert S. Macon
*Attorney, Agent, or Firm*—Quarles & Brady

[57] ABSTRACT

A switch has contacts constructed so that an electro-dynamic force is created by the current flowing through the switch which tends to maintain the switch in a closed state. This force counteracts other electro-dynamic forces which tend to open the switch. The contact design is particularly adapted from use in a single pole-double throw switch having a contact arm that is movable between two fixed contacts. The electro-dynamic force compensation exists between the contact arm and whichever one of the fixed contacts the contact arm is against. The fixed contacts also include arc runners so that any arc that develops as the contacts separate eliminates electro-dynamic force which tends to maintain the switch in a closed state.

17 Claims, 4 Drawing Sheets

FIG. 4
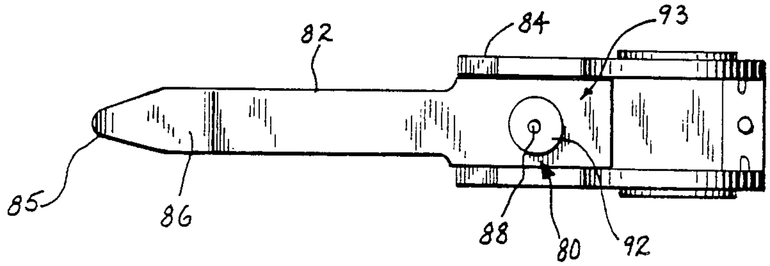
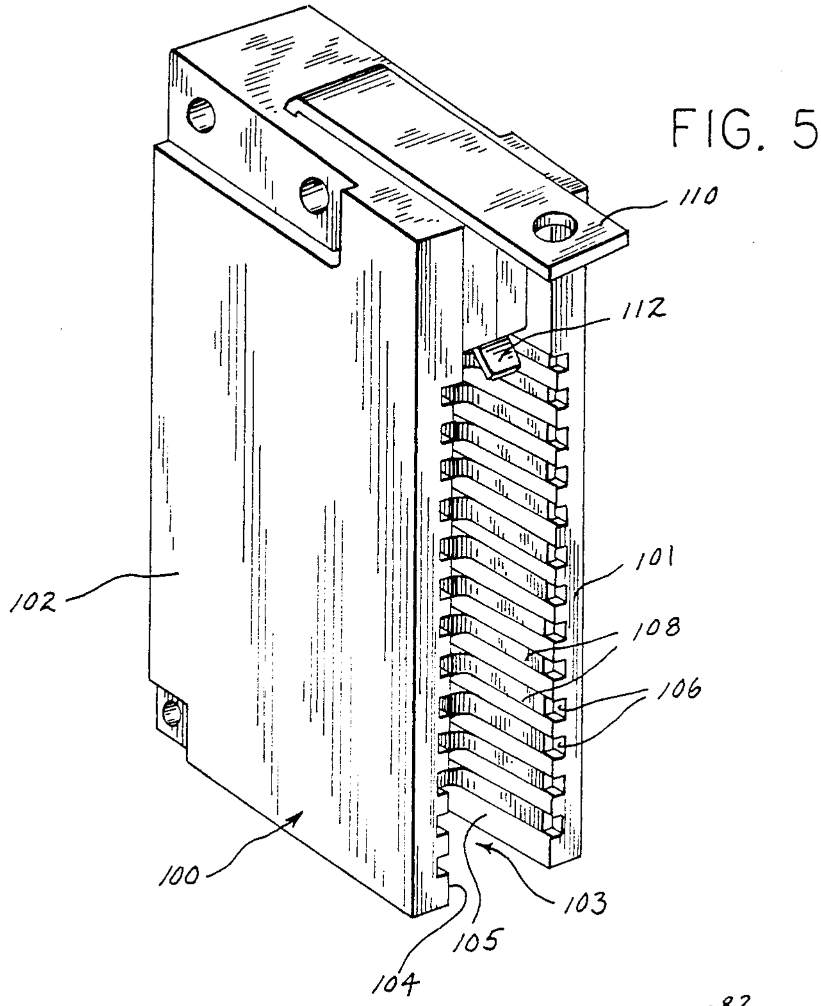
FIG. 5
FIG. 6
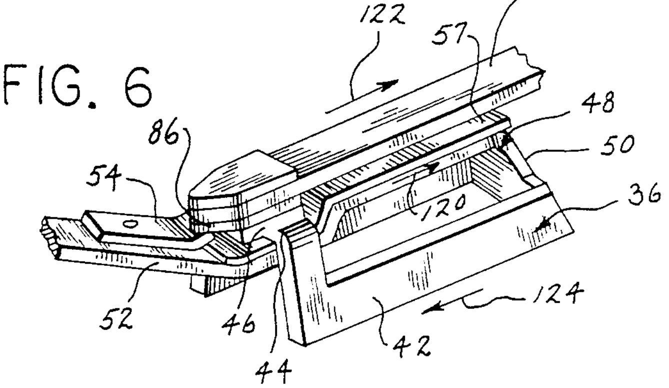

ELECTRIC SWITCH WITH COUNTERACTING ELECTRO-ELECTRO-DYNAMIC FORCES

The present invention relates to electric switches, and more particularly to electric switches that are designed to utilize electro-dynamic forces to keep the contacts closed.

BACKGROUND OF THE INVENTION

Electrical load transfer switches, such as shown in U.S. Pat. No. 4,034,170, are conventionally employed to switch an electrical load between a normal power supply, such as the utility company lines, and an emergency power supply, such as a stand-by diesel engine powered generator. Such devices are typically incorporated into the electrical system of large buildings to operate elevators, emergency lighting and other equipment in the event of a failure of the electric utility company's power. The transfer switches either consist of separate interconnected single pole-single throw switches for the emergency and normal power sources or a single pole-double throw switch for each phase of the electric power being controlled.

Such transfer switches may either be manually operated or automatically controlled by an electric circuit that detects a fault in the normal electric power source. The control circuit senses an undervoltage condition or a complete lack of power from the utility company, for example, and energizes a solenoid or other mechanism activating the switch to connect the building's emergency circuits to a generator. The sensing circuitry may also automatically start the generator.

Because such devices typically must withstand relatively large electric currents, for example many thousand amperes under short circuit conditions, several electro-dynamic effects must be taken into account in the switch design. The first affect to be reckoned with is the constriction of the current path between the contacts of the switch. Large electric currents flow to and from the constriction in opposite directions, closely spaced to each other. This creates a force directly proportional to the square of the current flowing through the contacts which tends to move the switch contacts apart. In order to overcome this contact separation force, previous switch assemblies have incorporated large spring mechanisms to exert forces which counteract this force.

Another electro-dynamic force that has to be taken into account is the force from the magnetic fields that are established around the conductive elements of the switch. It is well known that currents flowing in opposite directions through two parallel conductors create electromagnetic fields having flux lines running in opposite directions. The opposed lines of flux tend to force the two parallel connectors apart. If a switch is designed with currents flowing in opposite directions through parallel contact arms, the electro-magnetic fields create a force which tends to separate the contacts. Heretofore, large spring assemblies have typically been incorporated into the switch mechanism to counteract these electro-magnetic forces.

These forces which tend to separate the contacts, commonly referred to as the "blow-off" force, have been used in circuit breakers to enhance the separation of circuit breaker contacts in the presence of excessive currents.

A corollary electro-magnetic force causes an attraction of two conductors when currents flow in the same direction through two parallel conductors. This attraction force has been used to hold the switch contacts together and is commonly referred to as a "blow-on" force. An example of a switch which takes advantage of the blow-on force is shown in U.S. Pat. No. 4,467,301. In that device, the fixed contacts are formed as part of a loop assembly so that a part of the final switch contact is parallel to the movable contact. The current flows in the same direction through the part of the fixed switch contact and the movable contact thereby creating a blow-on force. The blow-on force due to the electromagnetic fields is also proportional to the square of the current flowing through the switch. Therefore, the blow-on force is proportional to the blow-off force. These forces counteract each other in a properly designed switch mechanism which takes advantage of the blow-on forces. The result is that the contacts remain closed under a high fault current.

However, previous loop type blow-on switch contacts such as in U.S. Pat. No. 4,467,301 did not lend themselves to a single pole-double throw type mechanism as used in transfer switches.

SUMMARY OF THE PRESENT INVENTION

An electrical switch according to the present invention has a fixed contact with two spaced apart L-shaped members. A contact bridge extends from a short leg of one L-shaped member to a corresponding short leg on the other L-shaped member. A conductor arm has a first section attached to the long legs of each of the L-shaped members and extends substantially coplanar with the contact bridge in the preferred embodiment. The conductor arm has a second section contiguous with a first section and extending between the L-shaped members. Provision is made for attaching an electrical conductor to the second section. The switch has a movable contact arm which in the closed switch state is parallel to the first section of the conductor arm.

A general object of the present invention is to provide a switch in which the electrical currents flowing through the contact assembly create an electro-dynamic force which tends to hold the switch contacts closed.

Another object of the present invention is to provide a fixed switch contact which maximizes the electro-dynamic force that tends to maintain the switch in the closed state while minimizing the electro-dynamic force which tends to separate the contacts from the closed state.

Another object of the present invention is to provide an arc runner on the fixed contact of the switch to prevent an arc created as the contracts separate from being exposed to an electro-dynamic force which counteracts the force driving the arc into the arc chamber.

An additional object of the present invention is to create a small blow-off force at the point of contact between the movable and fixed contacts. This provides a force to blow an arc into an arc chamber when the contacts separate. The small blow-off force is couteracted when the contacts are closed by the larger blow-on force.

A further object of the present invention is to provide a switch assembly for an automatic transfer switch having two fixed contacts and a movable contact that alternately engages one of the two fixed contacts. This switch assembly being so designed so that both sets of fixed contacts create counteracting electrodynamic forces.

Another object of the present invention is to provide a make-before-break single pole-double throw switch embodiment that has contacts that create counteracting electrodynamic forces.

BRIEF DESCRIPTION OF THE DRAWINGS

FIG. 4 is a plane view of the movable contact arm assembly shown in FIG. 2.

FIG. 5 is a perspective view of the arc chute shown in FIG. 2.

FIG. 6 is a perspective view of a fixed contact and the movable contact in the closed state.

DETAILED DESCRIPTION OF THE PREFERRED EMBODIMENT

Figure 1:
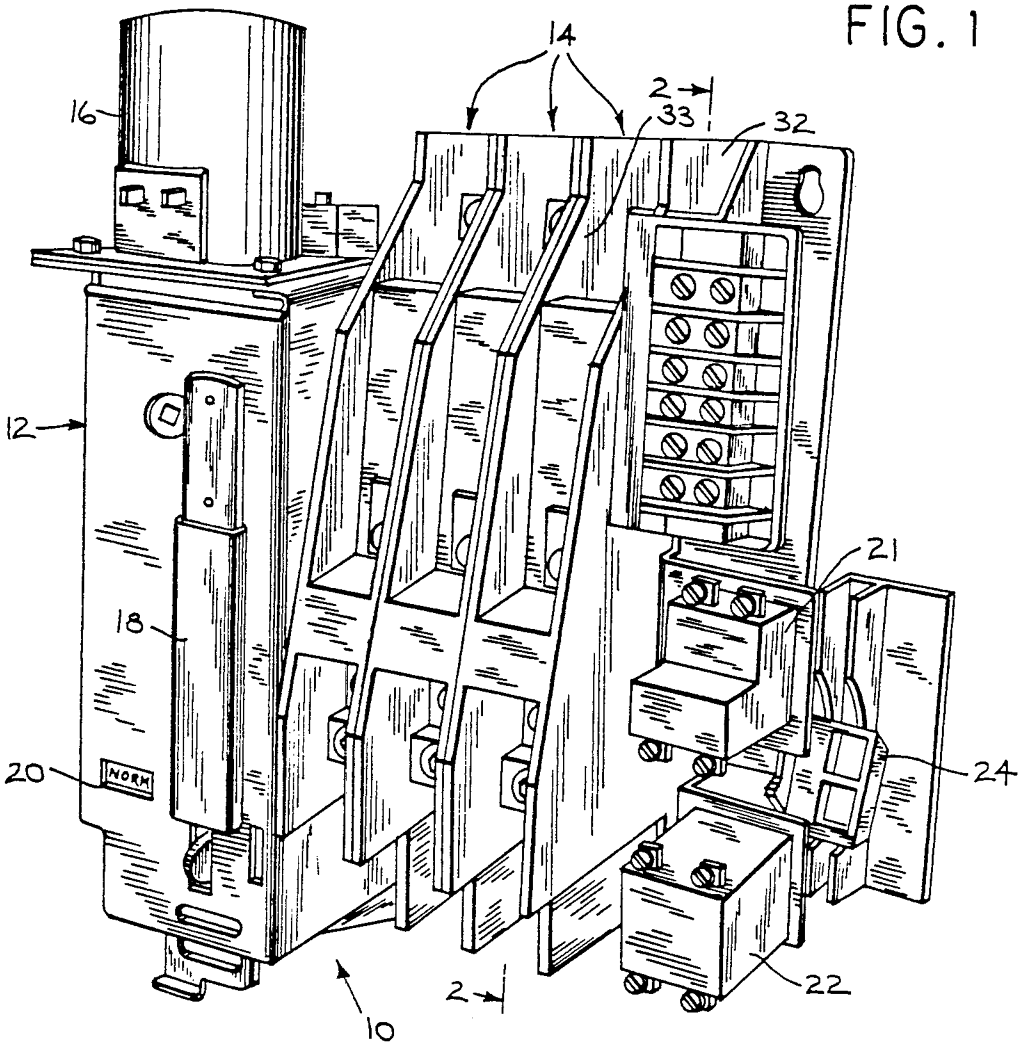
FIG. 1 is view of an automatic transfer switch having switch modules that incorporate the present invention.

With initial reference to FIG. 1, an automatic transfer switch for connecting an electric load either to a normal power source or an emergency power source is generally designated 10. The transfer switch 10 has a drive assembly 12 and in this embodiment three switch modules 14. One switch module 14 is provided for each phase of a three phase electrical power system. The exact number of switch modules 14 that are provided on the transfer switch 10 is a matter of design choice depending upon the number of electric lines being switched and the magnitude of the currents through each of the lines. The drive assembly 12 includes a solenoid 16 for electrically operating the three switch modules 14 and a lever 18 for manually operating the switch. The solenoid may be operated by a conventional fault sensing circuit. A position indicator 20 is provided on the drive assembly 12 to indicate which of the two power sources is connected to the load.

Two sets of auxiliary switches 21 and 22 are provided on the transfer switch 10. These auxiliary switches 21 and 22 are activated by a teeter bar 24 that is connected to a switch shaft 68 (FIG. 2) which runs between the teeter bar 24 and the drive assembly 12 through each of the switch modules 14. The switch shaft 68 is rotated by the drive assembly 12 to switch the load to different power sources. The teeter bar is in one of two positions depending upon whether the emergency or the normal power source is connected to the equipment. The teeter bar 24 activates one of the sets of auxiliary switches 21 or 22 depending upon the position of the drive shaft, and therefore the position of the switches within modules 14. This activation of the auxiliary switches 21 and 22 provides a signal to the fault sensing circuitry indicating the position of the transfer switch 10.

Figure 2:
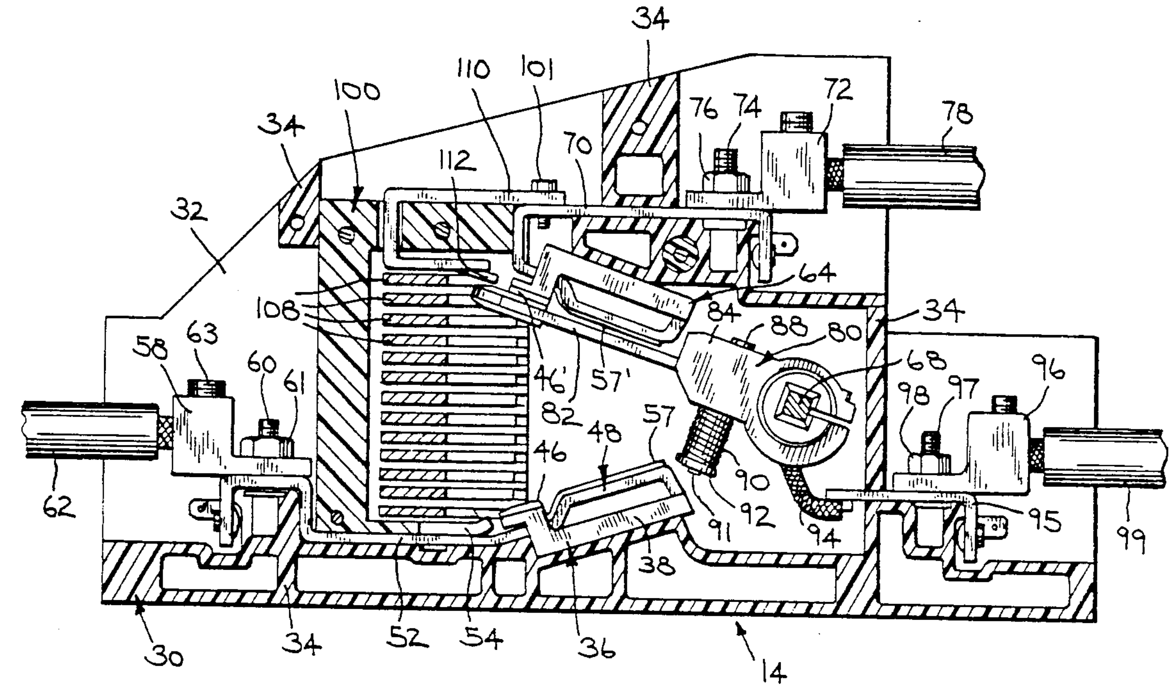
FIG. 2 cross sectional view of one of the switch modules in FIG. 1.

The interior mechanism of one of the switch modules 14 is illustrated in FIG. 2. The switch module 14 includes a housing 30 that includes a wall 32. The housing 30 is formed of a non-conductive material, such as plastic. A number of internal support ribs 34 extend from the first wall 32 and provide separation of the first wall 32 from a parallel second wall 33 (FIG. 1) that has been cut away in the cross section of FIG. 2. The support ribs 34 also provide support for the various internal components of the switch assembly to be described. In addition, grooves are provided on the interior surface of the first and second walls 32 and 33 to receive the edges of the various internal components to further provide their support.

Figure 3:
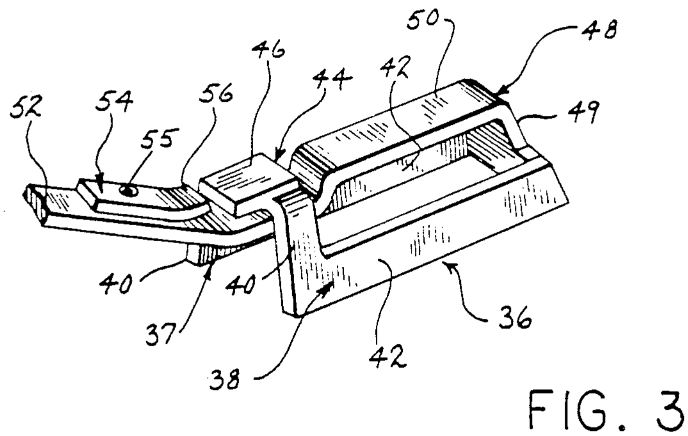
FIG. 3 is a perspective view of one of the fixed contacts shown in FIG. 2.

Located within the switch 14 is a first fixed contact 36, which is shown in detail in FIG. 3. The first fixed contact 36 is formed of electrically conductive material and has two spaced apart L-shaped members 37 and 38. Each L-shaped member 37 and 38 has a short leg 40 and a long leg 42 with an end of each joined together. Extending between the distal ends of the two short legs 40 is a bridge member 44 so as to form a U-shaped contact section with each of the short legs 40. On the outer surface of the bridge member 44 is an electrical contact pad 46.

The first fixed contact 36 also includes an elongated conductor arm 48 having an end section 49 connected between the distal ends of each of the long legs 42. Extending at essentially a right angle from the end portion 49 is a first section 50 of the conductor arm 48. This first section 50 is substantially coplanar with the bridge member 44. A second section 52 of the conductor arm 48 extends from the first section 50 bending under the bridge member 44 and between the two short legs 40. The second section 52 then continues to extend away from the bridge member 44. When the fixed contact 36 is positioned in the housing 30 as shown in FIG. 1, a sheet of electrically non-conductive material 57 is placed between the bridge member 44 and the conductor arm 48 and along the first section 50 of the conductor arm. The sheet 57 prevents the conductor arm 48 from contacting the bridge member 44.

An arc runner 54 of conductive material is attached to the second section 52 of the conductor arm 48 by a rivet 55. The arc runner 54 has an end portion 56 that is bent away from the conductor arm 48 so as to extend toward the contact pad 46 and be closely spaced therefrom. As shown in FIG. 2, the end of the second conductor arm section 52 which is remote from the first section 50, has a first cable clamp 58 attached to it by a threaded terminal stud 60 and nut 61. The first cable clamp 58 is a conventional device that includes an aperture into which the conductor of a first electrical cable 62 is fastened by a set screw 63. The first electrical cable 62 carries current from a first power source (not shown).

With continuing reference to FIG. 2, a second fixed contact 64 is also located within the switch module 14. The second fixed contact 64 is similar to the first contact 36 but is in an inverted position within the switch assembly with respect to the first fixed contact. The first and second fixed contacts 36 and 64 are positioned so that the surfaces of their contact pads 46 lie on different radii from the center of the switch shaft 68 extending through the module housing 30. The second section 70 of the conductor arm of the second fixed contact 64, however, is bent back looping over the top of the second fixed contact. The second section 70 has a second cable clamp 72 attached to it by a threaded terminal stud 74 and associated nut 76. The conductor of a second electrical cable 78 is fixedly held within the second cable clamp 72. The second electrical cable 78 carries current from a second power source (not shown).

Attached to the square switch shaft 68 is a movable contact assembly 80 that includes a movable, electrically conductive contact arm 82 attached to a shaft clamp 84. The clamp 84 is fixedly coupled to the switch shaft 68. As noted previously, the switch shaft 68 extends through the switch module 14 from the drive assembly 12 (FIG. 1). The movable contact assembly 80 pivots within the housing 30 as the switch shaft 68 is rotated by the drive assembly 12. The contact assembly 80 pivots between the position shown in FIG. 2 and a second position where its contact arm 82 abuts the first fixed contact 36.

FIG. 4 shows a planar view of the underside of the movable contact assembly 80 and should be referred to along with FIG. 2 with respect to the following description. One end 85 of the contact arm 82 has a contact pad 86 on each of its major surfaces. These contact pads 86 mate with the contact pads 46 on the fixed contacts 36 and 64, depending upon the position of the contact assembly 80. This mating completes an electric path between the movable contact arm 82 and the corresponding fixed contact. The shaft clamp 84 has a channel-like depression 85 on its underside in which the other end of the movable contact arm 82 is held. An elongated rivet 88 extends through the upper surface of the shaft clamp 84 and through an aperture in the contact arm 82. A compression spring 90 is located around the elongated rivet 88 between its lower end 91 and the immovable contact arm 82. A washer 92 holds the spring 90 on the elongated rivet 88. This attachment of the contact arm 82 to the shaft clamp 84 allows a pivoting movement between the contact arm 82 and the shaft clamp 84 when rotational force is exerted on the clamp by the shaft 68 after the contact arm 82 has engaged one of the fixed contacts 36 or 64.

A wire braid conductor 94 is spot welded to the contact arm 82 in a region designated by arrow 93 on FIG. 4. The wire braid conductor 94 is also spot welded to a terminal conductor 95. A third cable clamp 96 is attached to the terminal conductor 95 by a threaded terminal stud 97 and associated nut 98. The conductor of a third electrical cable 99 is held within the cable clamp 96 and couples the switch 10 to an electrical load (not shown).

With reference to FIGS. 2 and 5, also located within the switch module 14 is a arc chute 100. The arc chute 100 consists of a housing 102 of a non-conductive material such as a plastic. The chute housing 102 has an elongated U-shaped opening 103 on one of its edges 101 within which opening the contact arm 82 moves when rotated by shaft 68. Each inner surface 104 and 105 which defines the U-shaped opening 103 has thirteen parallel grooves 106 extending perpendicular to edge 101. Located within the grooves 106 are thirteen parallel U-shaped deion plates 108 formed of conductive and magnetic material, such as steel. The number of grooves 106 and hence plates 108 is a matter of design choice depending upon the physical dimensions of the arc chute 100, the voltage and current of the electricity being switched. The distance between the legs of the U-shaped deion plates is selected to allow the movable arm 82 to pass therebetween as it rotates between the first and second fixed contacts 36 and 64.

At one end of the arc chute 100, the top end as shown in FIGS. 2 and 5, is a second conductive arc runner 110. The second arc runner 110 has a tab 112 extending from it substantially coplanar with the contact pad 46' on the second fixed contact 64. The arc runner tab 112 is closely spaced from contact pad 46' and the movable arm 82 when the arm is in contact with the second fixed contact 64. The arc runner 110 is mechanically and electrically coupled to the second section 70 of the second fixed contact 64 by a bolt 101. This mechanical connection also holds the arc chute 100 within the switch module 14. By removing the bolt 101, the arc chute 100 may be removed to allow visual inspection of the contact pads on each of the fixed contacts 36 and 64 as well as the movable contact arm 82.

With reference to FIG. 2, the switch shaft 68 is rotated by the drive assembly 12 moving the electrical contact arm 82 between the two fixed contacts 36 and 64. In the position illustrated by FIG. 2, the movable contact arm 82 is in electrical contact with the second fixed contact 64 so that the current applied to the switch module 14 via the second cable 78 is coupled to the third cable 99 going to the load. When the switch shaft 68 rotates the contact assembly counter-clockwise from the position shown in FIG. 2, the contact arm 82 will strike the first fixed contact 36. In this latter position the current supplied by the first cable 62 is fed to the third cable 99.

One of the problems often encountered in switching high voltage electricity is arcing between the contacts as they separate. If this arc is not quenched when the movable contact arm 82 connects to the other fixed contact, the arc will provide an undesirable electrical coupling between the two power sources. The arc chute 100 provides a quenching mechanism for any arc that may form between the contacts as they separate. Such a mechanism and its operation are well known in the art. Specifically, as the contacts separate the arc is divided into individual arclets between the various deion plates 108 in chute 100. As the movable contact arm 82 travels farther and farther from the fixed contact to which it was previously connected, more and more deion plates are in the path of the arc. Eventually the electrical potential between adjacent deion plates 108 drops to a level at which the arclet can no longer be maintained thereby extinguishing the arc before the movable contact arm 82 reaches the other fixed contact.

Each of the present fixed switch contacts 36 and 64 is designed to create an electro-dynamic force which counteracts the force created by the contact current path constriction. As shown in FIG. 6, when a movable contact arm 82 is against the first fixed contact 36, the contact pads 46 and 86 are touching. A small gap exists between the conductor arm contact pad 86 and the arc runner 54. The movable contact arm 82 is spaced close and parallel to the first section 50 of the conductor arm 48. In this position, the electric current from one of the power sources supplied via cable 62 flows through the conductor arm 48 in a direction indicated by arrow 120. This current then flows from the conductor arm 48 into and through the two L-shaped members 37 and 38 on each side of the first fixed contact 36 in the direction indicated by arrow 124. The divided currents flow from each L-shaped member 37 and 38 into the bridge 44 and contact 46. The current is recombined and flows from the contact pad 46 to the contact pad 86 on movable arm 82. This current then flows in direction indicated by arrow 122 through the contact arm 82 and its terminal assembly ultimately to the load cable 99 (FIG. 2).

As indicated by arrows 120 and 122, the current flows in the same direction through the adjacent portions of the movable contact arm 82 and the conductor arm 48 of the fixed contact 36. The current flow in each of these elements produces electro-magnetic fields in which the flux lines are oriented so as to create an electro-dynamic force of attraction which tends to pull the contact arm 82 and the conductor arm 48 together. This force of attraction tends to hold the two contact pads 46 and 86 together and the switch in the existing closed state. The attraction force counteracts the force due to the current path constriction which tends to push the two contact pads 46 and 48 apart opening the switch. As both of these forces are proportional to the square of the current through the contacts, they counteract each other regardless of the current's magnitude.

Although the current flow through the L-shaped members 37 and 38 is in the opposite direction to the current flow in the movable arm 82, the repulsive forces created by their opposing electromagnetic fields is minimized. First, the L-shaped members 37 and 38 are more remote from the movable contact arm 82, than the conductor arm 48. Secondly, the current flow from the conductor arm 82 is divided in half as it passes through each of the L-shaped members. Thirdly, the L-shaped members 37 and 38 are positioned on the sides of the movable contact arm 82. The unique design of the present fixed contacts 36 and 64 maximizes the effects of the electro-dynamic forces of attraction while minimizing the electro-dynamic forces of repulsion associated with each fixed switch contact 36 and 64.

Therefore, a smaller force has to be exerted on the movable contact assembly 80 to keep the contact resistance in agreement with the resistance required for the rated current of the switch. This structure also eliminates the necessity to provide relatively large springs as in certain previous devices to maintain the switch in a closed state during high current conditions. These counteracting electro-dynamic forces maintain the switch in a closed state in the presence of a short circuit until a protective device such as a fuse or a circuit breaker can activate. In addition, the unique design of the fixed switch contacts 36 and 64 allows their use with a movable contact arm 32 to form a single pole-double throw switch for an automatic transfer device.

Figure 7:
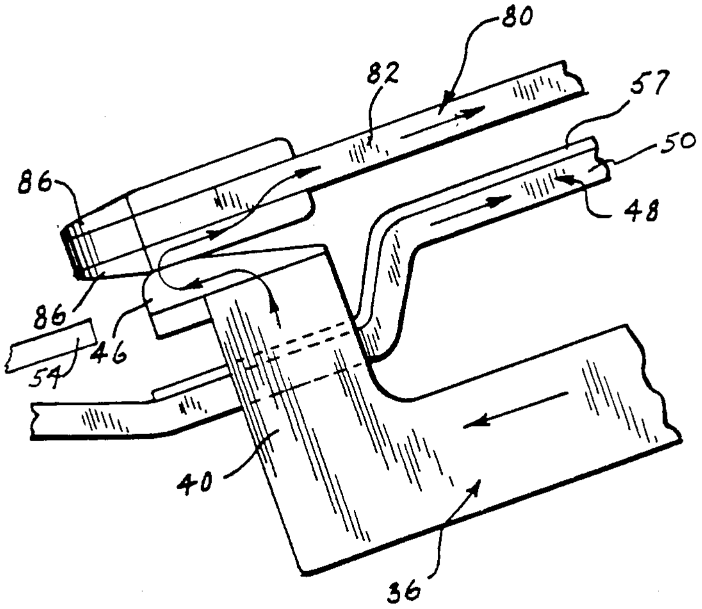
FIG. 7 is an enlarged portion of FIG. 6 illustrating the contact surfaces.

With reference to FIG. 6 and 7, as the contact arm 82 moves away from the fixed contact pad 46 as the switch opens, an electric arc may be created between the former points of contact of these two elements. The current due to the arc continues to flow through the contacts along the path illustrated by the arrows in FIG. 7. The current flows in substantially opposite directions for a short distance in the contact pads 46 and 86. When the contacts were closed, the electro-dynamic force of repulsion created by this opposite current flow was significantly less than the larger electro-dynamic force of attraction due to the current flow in arms 48 and 82. However, the close proximity of the repulsive force to the electric arc aids in blowing the arc from the fixed contact pad 46 onto the arc runner 54 and in blowing the arc into a loop that is within the arc chamber 100. Once the arc moves from the fixed contact pad 46 onto the arc runner 54, electric current no longer flows through the L-shaped members 37 and 38 or the conductor arm section 50 of the first fixed contact 36. Thus, the arc runner 54 creates a shunt path which extinguishes the electrodynamic force of attraction. This electro-dynamic force of attraction opposed the forces that blow the arc into the arc chamber 100, and tends to draw the arc away from the arc chamber. The extinction of the electro-dynamic force of attraction also enables the rotational force exerted on the contact arm 82 by drive shaft 68 in FIG. 2 to separate more easily the two switch contacts than if the arc maintained a current through the first section 50. The second fixed contact 64 and its arc runner 110 function in a similar manner.

While the structure of the switch module shown in FIG. 2 can control currents up to about 600 amperes, higher currents require a module with separate sets of arcing contacts and main contacts. Such devices are presently available in which the arcing contacts make before and break after the making and breaking of the main contacts. The arcs occur between the arcing contacts in these switches and not the main contacts. Therefore, the main contacts are not eroded by the arcs. The present contact structure, which utilizes the electro-dynamic forces to hold the contacts together, can be used as the arcing contacts in such high current switches.

Figure 8:
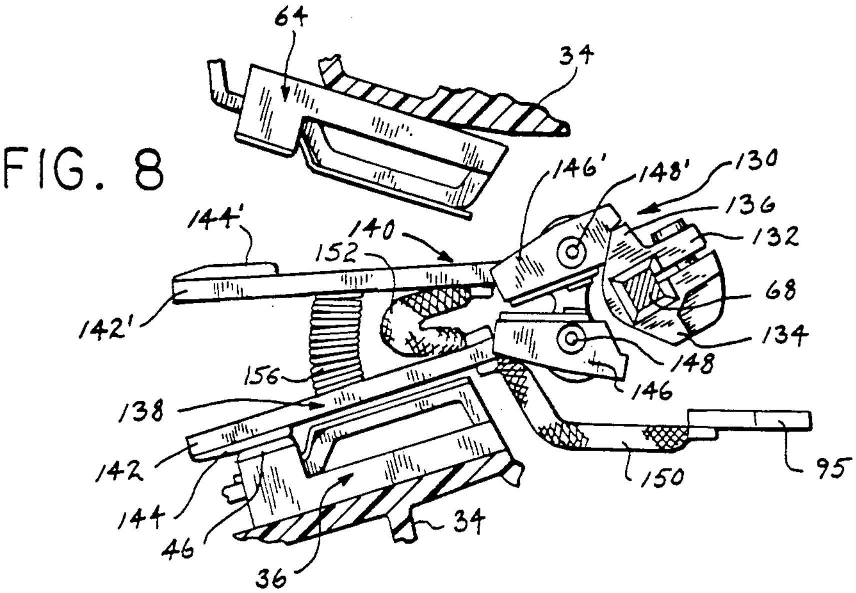
FIGS. 8–10 illustrate an alternative movable contact assembly in positions of its operation.
Figure 9:
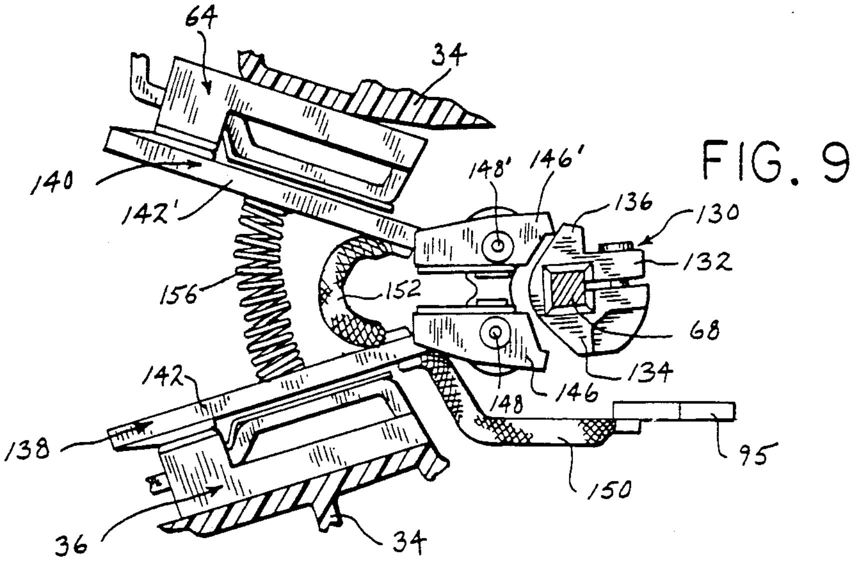
Figure 10:
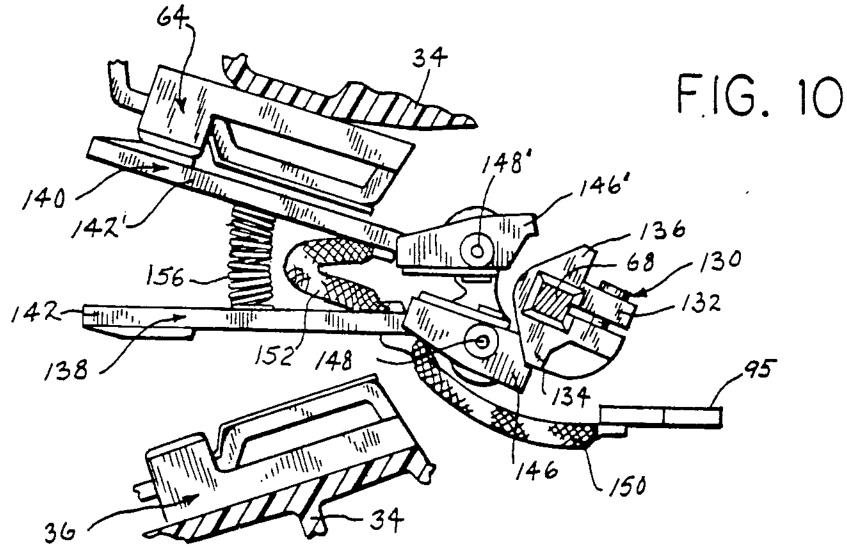

FIGS. 8–10 show an alternative movable contact assembly 130 which may be incorporated in a switch module 14 in place of the movable contact assembly 80 shown in FIG. 2. Elements associated with the alternative embodiment that are identical to elements of FIG. 2 have the same reference numerals. The alternative movable contact assembly 130 provides a make-before-break type switch. Such an assembly can be incorporated as a fourth switch module 14 on the transfer switch 10 in FIG. 1 to switch the neutral connection of a three-phase four-wire electrical system. In this variation, the transfer switch 10 simultaneously connects the neutral lines from both the normal and emergency sources to the load for a brief moment when the power is switched from one source to the other.

Referring once again to FIG. 8, the make-before-break contact mechanism 130 includes an actuator 132 that is clamped around the switch shaft 68 so as to rotate with the shaft. The actuator 132 has first and second drive tabs 134 and 136 located on opposite sides.

The make-before-break contact assembly 130 also includes first and second identical contact arm assemblies 138 and 140. The first contact arm assembly 138 will be described in detail with corresponding elements on the second contact arm assembly 140 being designated by the primed reference numerals of the elements described with respect to the first contact arm assembly. The first arm assembly 138 consists of a first electrically conductive arm 142 attached to a first arm rocker 146 formed of electrically insulative materials. The first arm rocker 146 is pivotally held within the switch housing 30 by a shaft 148. In the illustrated position, the arm rocker 146 for the first contact arm assembly 148 is pivoted so that a contact pad 144 at the distal end of the first contact arm 142 abuts the contact pad 46 of the first fixed contact 36. A spring 156 extends between the arm rockers 146 and 146' to pivotally bias the contact arm assemblies 138 and 140 apart so that the first contact arm 142 abutts the first fixed contact 36.

As shown in FIG. 8, the actuator 132 has been rotated by the switch shaft 168 so that its second drive tab 136 has engaged the rocker arm 146' for the second contact arm assembly 140. This engagement by the actuator 132 has pivoted the second contact arm assembly 140 against the bias of the spring 156 mechanism to rotate the assembly away from the second fixed contact 64.

A braided conductor 150 extends between the terminal conductor 95 and the first contact arm 142 and is spot welded to the terminal conductor and the contact arm. Another braided conductor 152 extends between and is spot welded to the contact arms 142 and 142' of the first and second contact arm assemblies. The first and second braided conductors 150 and 152 provide an electrical interconnection of the two contact arms 142 and 142' and the terminal conductor 95. Negligible current flows through the spring 156 due to its high resistance compared to the second braided conductor 152 or due to it being electrically insulated from the contact arms. In the position of the make-before-break contact assembly 130 depicted in FIG. 8, the power applied to the switch assembly by the first cable 62 to the first fixed contact 36 is coupled by the terminal conductor 95 to the load cable 99.

When the automatic transfer switch 10 is energized to transfer the connection to the load from one power source to the other, the drive assembly 12 rotates the switch shaft 68 in a counter-clockwise direction from the position illustrated in FIG. 8. As the shaft 68 and the actuator 132 coupled to it rotate, they reach an intermediate position shown in FIG. 9. In this position the actuator 132 no longer engages the second arm rocker 146' allowing the bias from the spring 156 to force the second contact arm 142' against the second fixed contact 64. In this intermediate position both contact arms 142 and 142' are engaging their respective fixed contact 36 and 64. At this point the first and second cables 62 and 78 are both electrically coupled to the third cable 99 going to the load.

Continuing rotation of the switch shaft 68 by the drive assembly 12 results in the actuator 132 engaging the arm rocker 146 of the first contact arm assembly 138. In this engaging position, the first drive tab 134 of the actuator 132 is forced against an angular surface of the rocker arm 146 of the first contact arm assembly 138 causing that rocker arm to pivot about its shaft moving the contact arm 142 away from contact with the first fixed contact 36 thereby breaking the electrical connection to the first cable 62 connected to the first fixed contact. During this continuing rotation, the second drive tab 136 of the actuator 132 moves away from engagement with the arm rocker 146' of the second contact arm assembly 140. Therefore, the continuing movement of the actuator 132 has no effect on the electrical contact that has been established between the second contact arm assembly 140 and the second fixed contact 64. When the rotation is complete, the make-before-break contact assembly 130 in the position shown in FIG. 10 and the load connect ed to the power source that is coupled to the second fixed contact 64.

The operation of the particular make-before-break contact assembly 130 of the present invention connects the neutral load line to the new power source before the phase lines of that power source are transferred by the other switch modules 14. The connection of the neutral load line to the previous power source is not broken until after the phase line connections have been broken. This make-before-break operation of the neutral line insures that any ground fault interrupters present in the load circuit will not trip due to the presence of a phase line connection without a neutral connection.

We claim:

1. An electrical switch comprising:

a fixed contact having two spaced apart L-shaped members, a contact bridge extending from a first leg of one L-shaped member to a first leg of the other L-shaped member, a conductor arm having a first section attached to a second leg of each L-shaped member and extending toward the contact bridge and said conductor arm having a second section contiguous with the first section, a portion of the second section extending between the L-shaped members; and a movable contact arm which in the closed state of the switch is in electrical contact with the contact bridge and extends adjacent to the first section of the conductor arm.

2. The switch as recited in claim 1 wherein the second section of the conductor arm includes means for connecting an electrical conductor to said fixed contact.

3. The switch as recited in claim 2 further comprising an arc runner electrically coupled to the second section of the conductor arm and positioned adjacent to the contact bridge.

4. The switch as recited in claim 1 wherein the first section of the conductor arm is substantially coplanar with said contact bridge.

5. The switch as recited in claim 1 further comprising means for quenching an electric arc which develops between said fixed contact and said movable contact arm.

6. The switch as recited in claim 5 wherein said fixed contact has a first contact pad on the contact bridge; and said contact arm has a second contact pad positioned to mate with the first contact pad; the contact pads being formed so that the direction of current flowing therethrough produce forces which blow any arc, formed therebetween, toward said means for quenching an electric arc.

7. A single pole - double throw switch comprising:

a contact assembly movable between first and second positions; and a first fixed contact positioned so that said contact assembly in the first position makes electrical contact with said first fixed contact, in the first position electric current flows through said contact assembly in substantially the same direction as electric current flows through a portion of said first fixed contact that is closely spaced from said contact assembly; and a second fixed contact positioned so that in said contact assembly in the second position makes electrical contact with said second fixed contact, in the second position electric current flows through said contact assembly in substantially the same direction as electric current flows through a portion of said second fixed contact that is closely spaced from said contact assembly.

8. The switch as recited in claim 7 wherein the first and second fixed contacts each compromises two spaced apart L-shaped members, a contact bridge extending from a first leg of one L-shaped member to a first leg of the other L-shaped member, a conductor arm having a first section attached to a second leg of each L-shaped member and extending toward the contact bridge and said conductor arm having a second section contiguous with the first section a portion of the second section extending between the L-shaped members.

9. The switch as recited in claim 8 further comprising two arc runners each being electrically coupled to the second section of a different conductor arm.

10. The switch as recited in claim 8 wherein the first section of the conductor arm of each fixed contact is substantially coplanar with the contact bridge for that fixed contact.

11. The switch as recited in claim 7 further comprising means for quenching an electrical arc which develops between the contact assembly and either fixed contact.

12. The switch as recited in claim 7 wherein said contact assembly comprises:

a first contact arm which makes electrical contact with said first fixed contact when the contact assembly is in the first position; and a second contact arm which makes electric contact with said second fixed contact when the contact assembly is in the second position;

said contact assembly having a third position in which the first contact arm makes electric contact with said first fixed contact and the second contact arm makes electric contact with said second fixed contact.

13. The switch as recited in claim 7 wherein at least one of said first and second fixed contacts further includes means for providing a conductive path for an arc existing between said fixed contact and said contact assembly, which conductive path shunts current from flowing through the portion of said fixed contact that is closely spaced from said contact assembly.

14. The switch as recited in claim 8 wherein the contact bridge of each of said fixed contacts includes a region through which the current flows in substantially the opposite direction to the direction of the current through the contact assembly when the contact assembly is in contact with the corresponding fixed contact.

15. A transfer switch, for connecting an electric load to either one of two power sources, comprising at least one switch assembly including:

first and second spaced fixed contacts, each of said fixed contacts having two spaced apart L-shaped members, a contact bridge extending from a first leg of one L-shaped member to a first leg of the other L-shaped member, a conductor arm having a first section attached to a second leg of each L-shaped member and extending toward the contact bridge and said conductor arm having a second section contiguous with the first section, a portion of the second section extending between the L-shaped members;

a movable contact arm having a first position in which it is in electrical contact with the contact bridge of the first fixed contact and adjacent to the first section of the first fixed contacts conductor arm, and a second position in which it is in electrical contact with the contact bridge of the second fixed contact and adjacent to the first section of the second fixed contact's conductor arm;

means for quenching an electric arc which develops between the movable contact arm and either fixed contact; and a drive means coupled to said movable contact arm for moving the arm between the two fixed contacts.

16. The transfer switch as recited in claim 15 wherein said means for quenching an electric arc comprises a series of spaced conductive plates located between the first and second fixed contacts.

17. The transfer switch as recited in claim 16 wherein said conductive plates are held in a housing that is removable from said switch assembly.

* * * * *

UNITED STATES PATENT AND TRADEMARK OFFICE
CERTIFICATE OF CORRECTION

PATENT NO. : 4,849,590

DATED : July 18, 1989

INVENTOR(S) : James A. Becker et al.

It is certified that error appears in the above-identified patent and that said Letters Patent is hereby corrected as shown below:

Title page and column 1, lines 2-3:

Change the title to --Electric Switch With Counteracting Electro-Dynamic Forces--.

Title page:

Change the assignee to Brown Industrial Gas, Inc., Dallas, Texas.

In Column 3, Line 9, after "is" insert --a perspective--.

In Column 3, Line 24, after "in" insert --three--.

Signed and Sealed this

Twenty-sixth Day of June, 1990

*Attest:*

HARRY F. MANBECK, JR.

*Attesting Officer*

*Commissioner of Patents and Trademarks*